US000002037H

(19) United States

(12) Statutory Invention Registration (10) Reg. No.: US H2037 H

Yates et al. (43) Published: Jul. 2, 2002

(54) ELECTROSURGICAL HEMOSTATIC DEVICE INCLUDING AN ANVIL

(76) Inventors: David C. Yates, 7534 Galway Ct., West Chester, OH (US) 45069; James W. Voegele, 11486 Kemperknoll, Cincinnati, OH (US) 45249; Jesse Kuhns, 3619 Michigan Ave., Cincinnati, OH (US) 45208; Anil Nalagatla, 341C Shawnee Run, West Carrollton, OH (US) 45449; Warren P. Williamson, IV, 101 Southbend Ct., Loveland, OH (US) 45140; Darrel M. Powell, 9447 Bainwoods Dr., Cincinnati, OH (US) 45249

(21) Appl. No.: 08/856,210

(22) Filed: May 14, 1997

(51) Int. Cl.[7] ..... A61B 18/18

(52) U.S. Cl. ..... 606/51

(58) Field of Search ..... 606/1, 41, 42, 606/45–52, 142, 143, 151, 205–207; 227/175.1, 180.1

(56) References Cited

U.S. PATENT DOCUMENTS

| | | | | |
|---|---|---|---|---|
| 3,898,992 A | | 8/1975 | Balamuth | |
| 4,655,216 A | | 4/1987 | Tischer | |
| 4,671,274 A | | 6/1987 | Sorochenko | |
| 4,777,949 A | * | 10/1988 | Perlin | 606/158 |
| 5,151,102 A | | 9/1992 | Kamiyama et al. | |
| 5,290,287 A | | 3/1994 | Boebel et al. | |
| 5,318,589 A | * | 6/1994 | Lichtman | 606/205 |
| 5,383,880 A | | 1/1995 | Hooven | |
| 5,389,098 A | | 2/1995 | Tsurtuta et al. | |
| 5,403,312 A | | 4/1995 | Yates et al. | |
| 5,465,895 A | | 11/1995 | Knodel et al. | |
| 5,597,107 A | | 1/1997 | Knodel et al. | |
| 5,653,721 A | * | 8/1997 | Knodel et al. | 606/151 |
| 5,720,742 A | * | 2/1998 | Zacharias | 606/1 |
| 5,735,848 A | * | 4/1998 | Yates et al. | 606/50 |

FOREIGN PATENT DOCUMENTS

| | | |
|---|---|---|
| EP | 0 640 315 A1 | 7/1993 |
| EP | 0 717 960 A2 | 6/1996 |
| EP | 0 737 446 A1 | 10/1996 |

* cited by examiner

*Primary Examiner*—Daniel T. Pihulic

(57) ABSTRACT

An electrosurgical instrument is provided for cauterization and/or welding of tissue of varying impedance, thickness and vascularity especially in the performance of endoscopic procedures. The instrument compresses the tissue between one pole of a bipolar energy source located on one interfacing surface, and a second interfacing surface applying pressure in a predetermined range wherein one of the interfacing surfaces is positioned on an anvil with a specified preload and spring rate. A second pole is located one of the two interfacing surfaces. In a preferred embodiment, the second pole is located on the same interfacing surface as the first pole and an insulator electrically isolates the two poles. A preferred application of the invention is in a cutting instrument wherein a hemostatic line is formed along a cut line using RF energy.

19 Claims, 12 Drawing Sheets

A statutory invention registration is not a patent. It has the defensive attributes of a patent but does not have the enforceable attributes of a patent. No article or advertisement or the like may use the term patent, or any term suggestive of a patent, when referring to a statutory invention registration. For more specific information on the rights associated with a statutory invention registration see 35 U.S.C. 157.

ELECTROSURGICAL HEMOSTATIC DEVICE INCLUDING AN ANVIL

FIELD OF THE INVENTION

This invention relates to an improved electrosurgical instrument and method for cauterization, coagulation and/or tissue welding in the performance of surgical procedures, especially endoscopic procedures.

BACKGROUND OF THE INVENTION

Surgical procedures requiring cutting of tissue can cause bleeding at the site of the cutting. Before surgeons had the means to control bleeding many surgical procedures were quite difficult to perform because of excessive blood loss. Hemostasis is even more crucial in endoscopic or laparoscopic surgery where if the bleeding is not kept under control, the laparoscopy must be abandoned and the patient's body cut to perform open surgery so that inaccessible bleeding may be controlled.

Thus, various techniques have been adapted to control bleeding with varying degrees of success such as, for example, suturing, applying clips to blood vessels, and stapling, as well as electrocautery and other thermogenic techniques. Advances in tissue joining, tissue repair and wound closure also have permitted surgical procedures previously not possible or too risky.

Initially, suturing was one of the primary means for providing hemostasis and joining tissue. Before other hemostatic and tissue repair means were introduced, surgeons had to spend a great deal of time sewing the tissue of patients back together.

Surgical clips were introduced as a means to close off blood vessels, particularly when cutting highly vascularized tissue. Application of surgical clips, however, can be cumbersome in certain procedures. The vessels must be identified. Then a clip must be individually applied on both sides of the intended cut of each identified vessel. Also, it may be difficult to find some vessels, particularly where the vessel is surrounded by fatty tissue.

Surgical staplers have been effective in decreasing the amount of time it takes to fasten tissue together. There are various types of surgical staplers. Staplers have been used for tissue joining, and to provide hemostasis in conjunction with tissue cutting. Such devices include, for example, linear and circular cutting and stapling instruments. Typically, a linear cutter has parallel rows of staples with a slot for a cutting means to travel between the rows of staples. This type of surgical stapler secures tissue for improved cutting, joins layers of tissue, and provides hemostasis by applying parallel rows of staples to layers of surrounding tissue as the cutting means cuts between the parallel rows. These types of cutting and stapling devices have been used successfully in procedures involving fleshy tissue such as muscle or bowel, particularly in bowel resection procedures. Circular cutting and stapling devices have successfully been used, for example, in anastomotic procedures where a lumen is rejoined. However, the results with cutting and stapling devices have been less than optimum where the procedure involves cutting highly vascularized tissue, such as mesentery or adnexa, which are prone to having hemostasis problems.

Electrocautery devices have also been used for effecting hemostasis. Monopolar devices utilize one electrode associated with a cutting or cauterizing instrument and a remote return electrode, usually adhered externally to the patient.

More recently, bipolar instruments have been used because the cauterizing current is generally limited to tissue between two electrodes of the instrument.

Bipolar forceps have been used for cutting and/or coagulation in various procedures. For example, bipolar forceps have been used in sterilization procedures where the fallopian tubes are sealed off. Generally, bipolar forceps grasp tissue between two poles and apply electrical current through the grasped tissue. Bipolar forceps, however, have certain drawbacks, some of which include the tendency of the current to arc between poles when tissue is thin or the forceps to short when the poles of the forceps touch. The use of forceps for coagulation is also very technique dependent and the forceps are not adapted to simultaneously cauterize a larger area of tissue.

Bipolar scissors have been disclosed where two scissors blades act as two electrodes having insulated shearing surfaces. This device mechanically cuts tissue as coagulating electrical current is delivered to tissue in the current path. Bipolar scissors are also highly technique dependent in their use.

In prior devices, such as the device described in U.S. Pat. No. 5,403,312, electrosurgical energy has been delivered to biologic tissue in order to create a region of coagulation, as, for example, on either side of an incision, thus preventing blood and other bodily fluids from leaking out of the incision. In such a device, if tissue grasped by the jaws is compressed too much by applying excessive pressure to the region of coagulation, the tissue grasped by the end effector may be torn or crushed. If the tissue is not compressed enough because to little pressure is applied to the region of coagulation, the tissue in the region of coagulation may not be not effectively or uniformly cauterized because fluid (e.g. blood) could remain in the region of cauterization. In prior art devices, the surgeon has used tactile feedback and visual clues to determine the amount of pressure to apply to the region in order to obtain optimum coagulation. In instruments wherein the region of coagulation is partially or fully obscured, either by the end effector or by tissue, and is, therefore, not visible to the surgeon, it is particularly difficult for the surgeon to ensure that the appropriate pressure is being applied by the end effectors to ensure proper coagulation. It would, therefore, be advantageous to develop an electrosurgical instrument wherein the surgeon is not required to adjust the pressure applied by the end effector prior to applying electrosurgical energy to tissue in the region of coagulation. It would further be advantageous to design an instrument wherein the pressure applied to the tissue prior to coagulation is within a predetermined range.

One known method of varying the pressure applied to the tissue by the jaws of the end effector involves varying the gap between the jaws depending upon the tissue being grasped. However, such an arrangement would necessitate the use of different instruments, different end effectors or different staple cartridges depending upon the tissue being grasped. It would, therefore, be advantageous to design an instrument wherein the pressure applied by the end effector would vary with the thickness and makeup of the tissue being grasped.

Non electrosurgical endocutters such as those described in U.S. Pat. No. 5,597,107, employ a relatively stiff lower jaw member which includes a staple cartridge in conjunction with a more flexible upper member which acts as an anvil against which the staples are formed. In such instruments, the anvil is generally manufactured to be as stiff as possible, within the limits of size, materials and other design considerations and the spring rate of such an anvil may be, for example, in the range of 350–450 pounds per inch. A stiff anvil helps to ensure that the staples form properly when the instrument is fired. Spring rate, in terms of tissue compression forces in conventional staplers with gap spacing pins, is used in conjunction with the gap pin to create and maintain a minimum gap between the staple cartridge and the anvil, setting the height of the formed staple. Therefore, the designers of conventional stapling instruments with gap spacing pins are primarily interested in the formation of a simple beam with consistent gap to form consistent staples. In other designs, the gap pin is not used and the anvil is designed with sufficient stiffness to facilitate the formation of tissue. It would, therefore, be advantageous to design an electrosurgical instrument where the spring rate of the anvil is sufficiently stiff for the formation of staples while exerting a pressure in a range which facilitates the proper cauterization of tissue.

SUMMARY OF THE INVENTION

It is therefore an object of the present invention to provide a hemostatic electrosurgical instrument which can exert pressure in a range to efficiently provide improved hemostasis in multiple tissue types and thickness, e.g., in fleshy or vascular tissue areas, and high, low or combination impedance tissues. Hemostasis is used herein to mean generally the arresting of bleeding including by coagulation, cauterization and/or tissue joining or welding.

Another object of the invention is to provide an improved cutting and stapling device with an electrocautery means for tissue welding or cauterization along a cutting path wherein the device is adapted to grasp tissue and exert a pressure within a predetermined range in order to provide improved hemostasis prior to cutting the tissue.

These and other objects of the invention are described in an electrosurgical device having an end effector with opposing interfacing surfaces associated with jaws for engaging tissue therebetween, and two electrically opposite poles located on one or both of the opposing surfaces. The poles are isolated from each other with an insulating material, or, where the poles are on opposite interfacing surfaces, they may be offset from each other so that they do not directly oppose each other on interfacing surfaces. In particular, an electrosurgical device according to the present invention includes a substantially fixed lower jaw. Further, an electrosurgical device according to the present invention includes a substantially flexible upper jaw having a spring rate in the range of between approximately 200 pounds per inch and approximately 600 pounds per inch. More particularly, the spring rate of the upper jaw is approximately 275 pounds per inch.

An electrosurgical instrument of a preferred embodiment compresses tissue to a pressure within a predetermined range in a compression zone between a first interfacing surface and a second interfacing surface and applies electrical energy through the compression zone. The first interfacing surface is comprised of: a first pole of a bipolar energy source, which interfaces with the compressed tissue in the compression zone; and a second pole electrically isolated from the first pole and located on the same or opposite interfacing surface. Electrically isolated poles are defined herein to mean electrodes isolated from each other by an insulating material in the end effector and/or offset from each other on opposing surfaces.

In a preferred embodiment, the compression zone is an area defined by a compression ridge on one of the interfacing surfaces which compresses the tissue against the other interfacing surface. Also, there may be a compression ridge on both interfacing surfaces. A coagulation zone is defined by the first pole, the second pole, and an insulator insulating the first pole from the second pole. The second pole, located on one of the interfacing surfaces, is generally adjacent to the insulator on the same interfacing surface or across from the insulator on an opposing surface. This arrangement electrically isolates the two poles and enables the current path between the first and second poles to cross through a desired area of tissue.

It is believed that the tissue compression normalizes tissue impedance by reducing structural differences in tissue which can cause impedance differences. Compression also stops significant blood flow and squeezes out blood which acts as a heat sink, particularly when flowing through blood vessels. Thus, compression optimizes delivery of energy to tissue in part by enabling the rate of energy delivery to exceed the rate of dissipation due to blood flow. The arrangement of the electrodes, which make up the poles, is important to ensure that the current passing between the two poles passes though the compression zone. Also, insulation or isolation of the opposite poles from each other on the instrument permits tissue compression without shorting of the instrument poles or electrical arcing common in bipolar instruments.

In one embodiment of the present invention, the pressure initially applied to tissue in the compression zone is between approximately 30 pounds per square inch (psi) and approximately 250 psi. In a further embodiment of the present invention, the pressure initially applied to tissue in the compression zone is between approximately 75 psi and 250 psi. In a further embodiment of the present invention, the pressure initially applied to tissue in the compression zone is between approximately 115 psi and 185 psi.

Thus, the tissue compression and the arrangement of the electrodes permit more efficient cauterization and offer the advantage of achieving hemostasis in a wide range of tissue impedance, thickness and vascularity.

In an alternative embodiment of the invention, the first pole is located on a first interfacing surface of a first jaw and the second pole is located on the same jaw as the first pole, but not on the interfacing surface.

The present invention also provides a device capable of coagulating a line or path of tissue along or lateral to a cut line or a cutting path. In one embodiment, the first pole comprises an elongated electrode. The elongated electrode along with the adjacent insulator form a ridge to compress the tissue to be cauterized. The second pole is adjacent the insulator on an opposite side of the insulator from the first pole.

In one preferred embodiment, a cutting means for cutting tissue is incorporated into the device and the device provides hemostatic lines adjacent to the path of the cutting means. Of course, cutting may occur at anytime either before, during or after cauterization or welding. In one variation of this preferred embodiment, stapling means is provided on one or both sides of the cutting path.

In one embodiment, an indicator means communicates to the user that the tissue has been cauterized to a desired or predetermined degree.

In another embodiment, the coagulation is completed prior to any mechanical cutting, i.e., actuation of the cutting means. If an indicator means is used, once tissue is cauterized, the cutting means may be actuated to cut between the parallel bars while the rows of staples are applied to the tissue.

In another embodiment, the hemostatic device is incorporated into a linear cutter similar to a linear cutting mechanical stapler. In this embodiment the hemostatic device comprises two parallel and joined elongated electrode bars which form one pole, and a slot for a cutting means to travel between the bars. Optionally, one or more rows of staples may be provided on each side of the slot and bars to provide additional hemostasis. In operation, tissue is clamped between two jaws. Electrical energy in the form of radio frequency current is applied to the compressed tissue to cauterize the blood vessels along the two parallel bars.

Another embodiment provides a means for detecting abnormal impedance or other electrical parameters which are out of a predetermined range. For example, the means for detecting may be used to indicate when the instrument has been applied to tissue exhibiting impedance out of range for anticipated good coagulation. It may also be used for detecting other instrument abnormalities. It is possible to detect the abnormal condition, for example, by using comparisons of normal ranges of initial tissue impedance in the interface electronics. This could be sensed in the first few milliseconds of the application of RF energy and would not present a significant therapeutic dose of energy. A warning mechanism may be used to warn the user when the impedance is out of range. Upon repositioning of the instrument, the same measurement criteria would apply and if the tissue impedance was again out of range, the user would again be warned. This process would continue until the normal impedance range was satisfied and good coagulation could be anticipated.

Similarly another embodiment provides a tissue welding and cauterizing cutting device similar to an intraluminal stapler. Preferably, the poles are formed in two concentric circle electrodes separated by an insulator. The electrodes which make up the poles may be located on either the stapler cartridge or the anvil.

In one embodiment of the present invention, the pressure exerted by the anvil is a function of the spring rate of the anvil. By providing a "pre-bend" angle on the anvil it is possible to obtain a pre-load (at a zero gap.) A preferred value of preload is in the range of between 12 and 18 pounds with a preferred value of approximately 15 pounds. In one embodiment of the present invention, the spring rate of jaw 32 is between approximately 225 pounds per inch and approximately 350 pounds per inch. More particularly , the spring rate of anvil 18 on jaw 32 is preferably in the range of approximately 275 pounds per inch.

These and other objects of the invention will be better understood from the following attached Detailed Description of the Drawings, when taken in conjunction with the Detailed Description of the invention.

DETAILED DESCRIPTION OF THE DRAWINGS

DETAILED DESCRIPTION OF THE PREFERRED EMBODIMENTS

Figure 1:
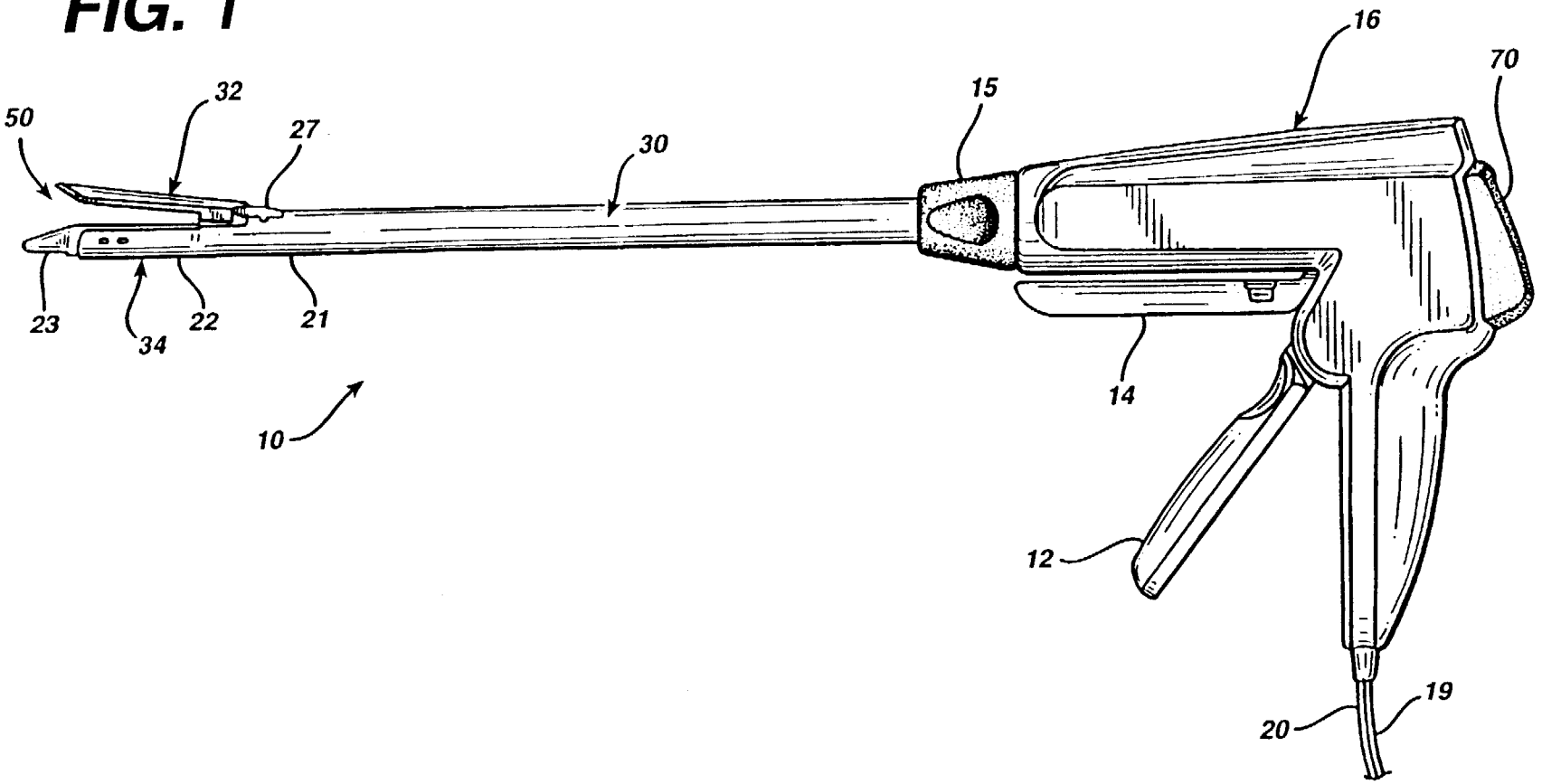
FIG. 1 is a side elevational view of an endoscopic electrocautery linear stapling and cutting instrument of one embodiment of the present invention.
Figure 2:
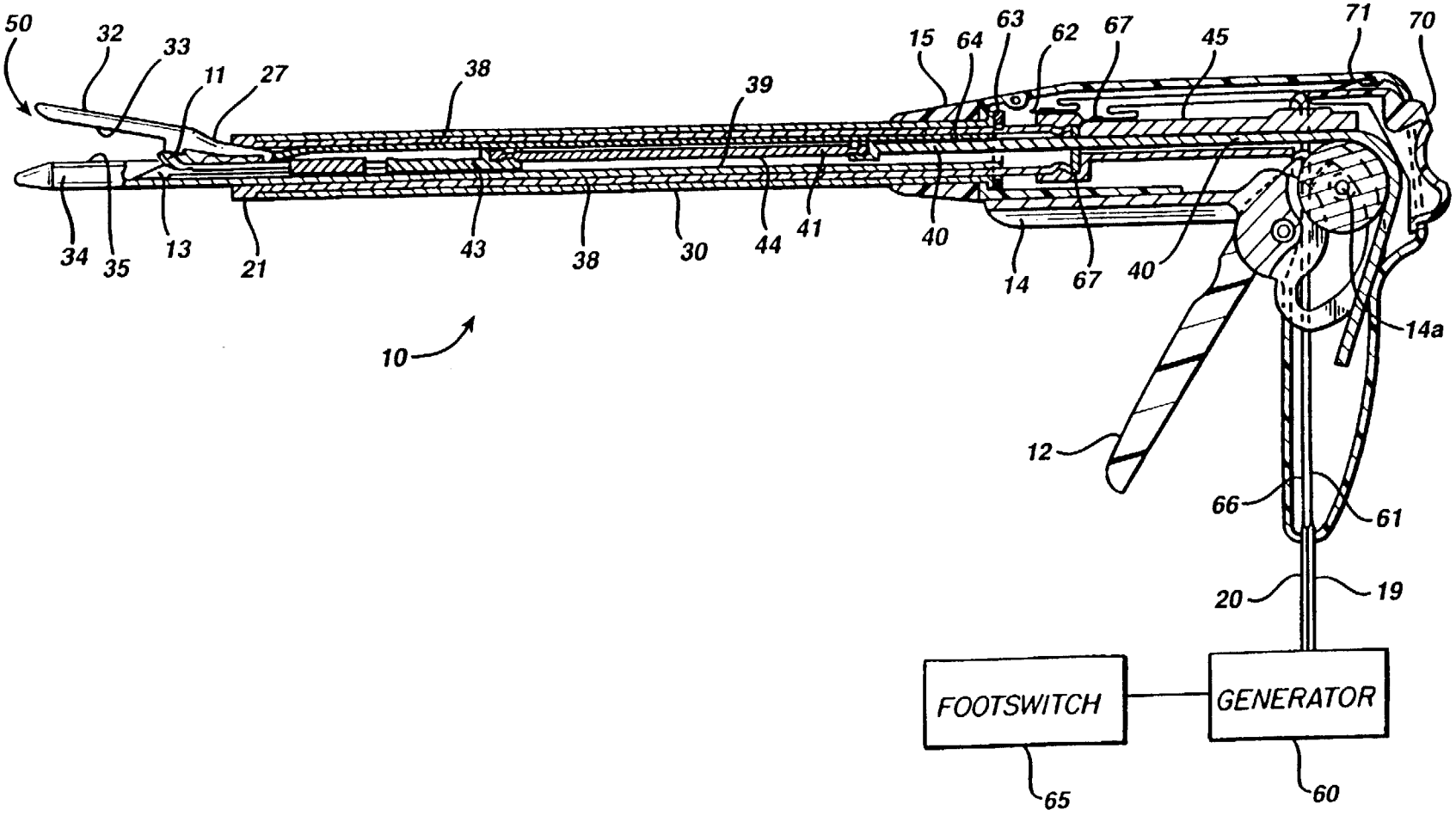
FIG. 2 is a side cross sectional view of the instrument of FIG. 1.
Figure 3:
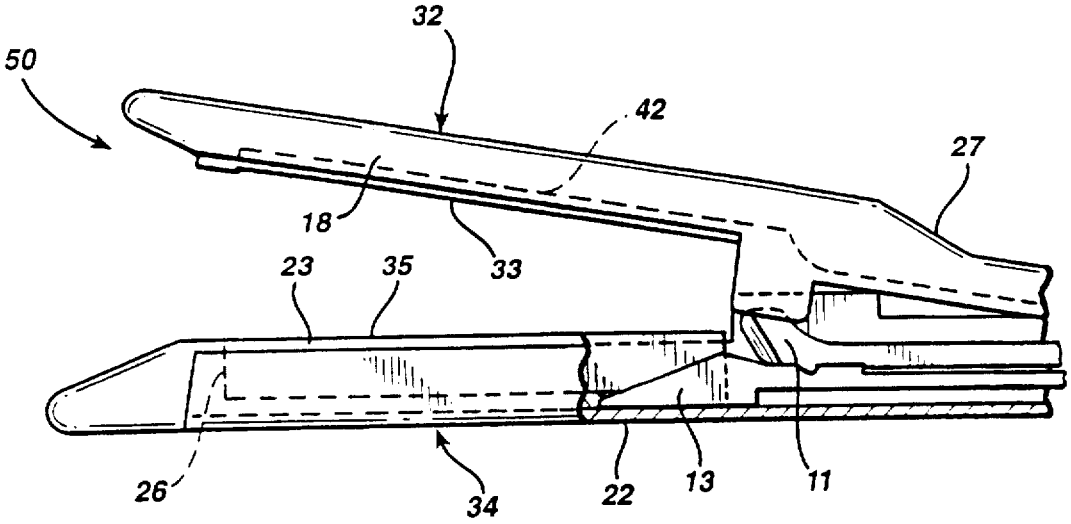
FIG. 3 is a partial cross sectional view of the distal end of the instrument of FIG. 1 in an open position.
Figure 4:
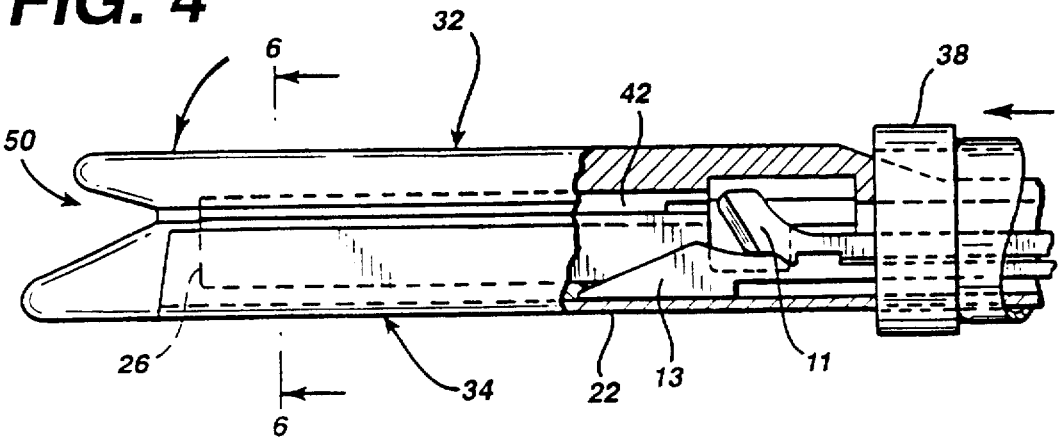
FIG. 4 is a partial cross sectional view of the distal end of the instrument of FIG. 1 in a closed, unfired position.
Figure 5:
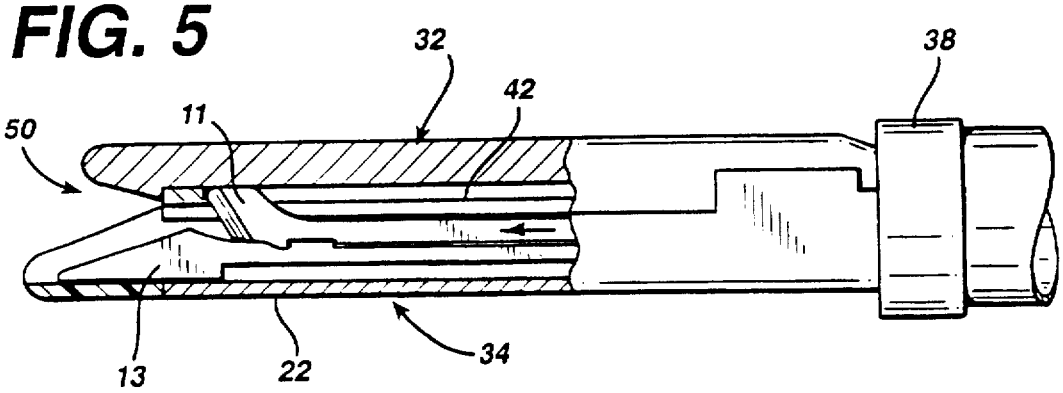
FIG. 5 is a partial cross sectional view of the distal end of the instrument of FIG. 1 in a closed, fired position.

Referring now to FIGS. 1–9, there is illustrated a preferred embodiment of the present invention. An endoscopic electrocautery linear cutting and stapling instrument 10 is shown having a body 16 coupled to a shaft 30 with a lumen extending therethrough and an end effector 50 extending from the distal end 21 of the shaft 30. The shaft 30 is formed of an insulative material and has an electrically conductive sheath 38 extending through its lumen. A channel 39 extending through the sheath 38 guides co-axial movement of a driver means 44 within the channel 39. In this particular embodiment, the driver means 44 includes a firing trigger 14 associated with the body 16, coupled to a flexible firing rod 40 coupled to a driving rod 41, coupled to a block 43. The block 43 is coupled to a cutting means 11 and a staple driving wedge 13, which the driving means 44 advances by way of the block 43 into the end effector 50.

The end effector 50 comprises two interfacing jaw members 32, 34. The end effector 50 is secured by way of jaw member 34 to the channel 39. The jaw member 32 is movably secured to jaw member 34. The body 16 has a clamping trigger 12 for closing the jaws 32, 34 which longitudinally advances a close rack 45 coupled to the proximal end of the sheath 38. The close rack 45 advances the sheath 38 co-axially through the shaft 30. The sheath 38 advances over a camming surface 27 of jaw 32 to close the jaws 32 and 34 onto tissue situated between the jaws. As described in more detail below, the close rack 45 also acts as a switch to close the circuit which communicates electrical energy to the end effector 50.

Figure 6:
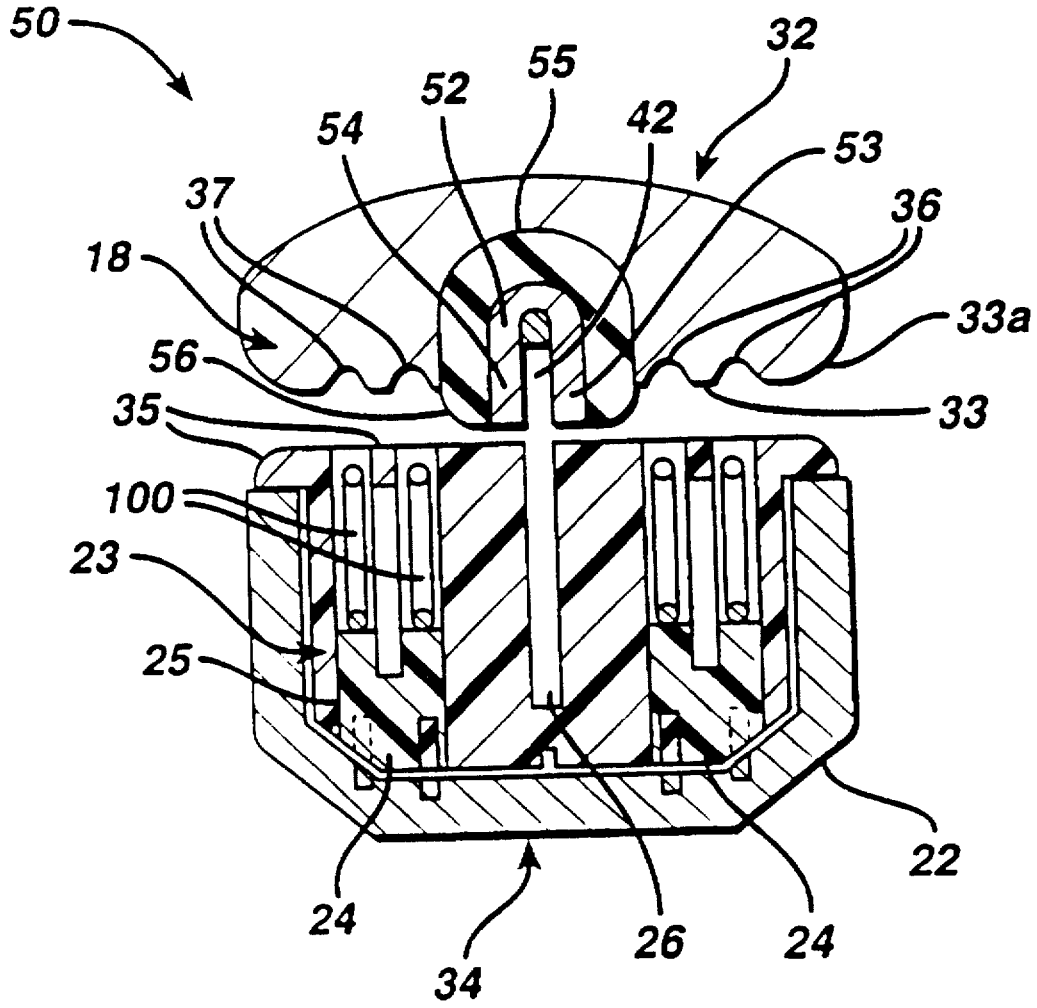
FIG. 6 is a front cross sectional view of the distal end of the instrument of FIG. 3 taken along the line 6—6.
Figure 7:
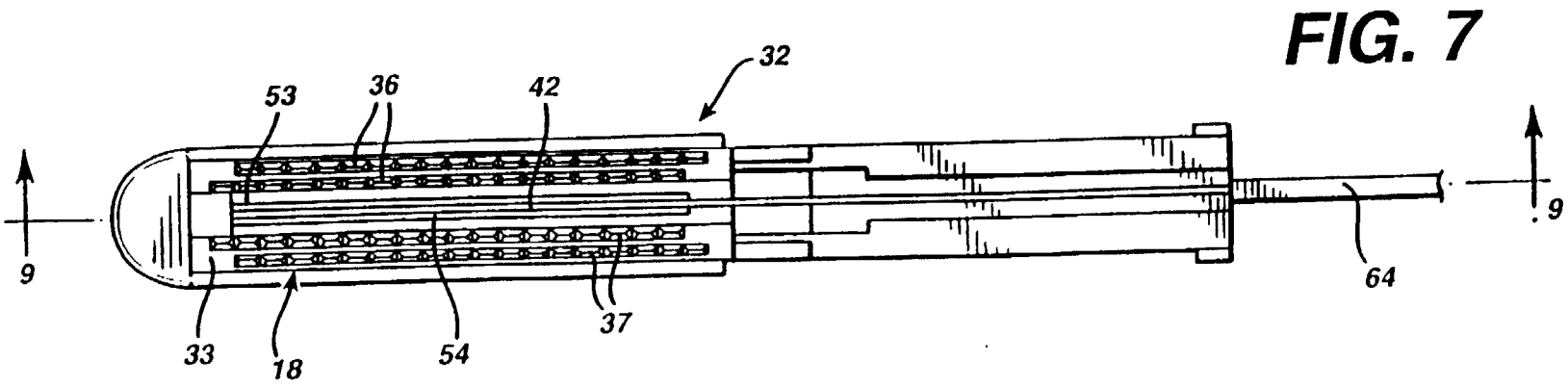
FIG. 7 is a bottom isolated view of the anvil jaw of the instrument of FIG. 1.
Figure 8:
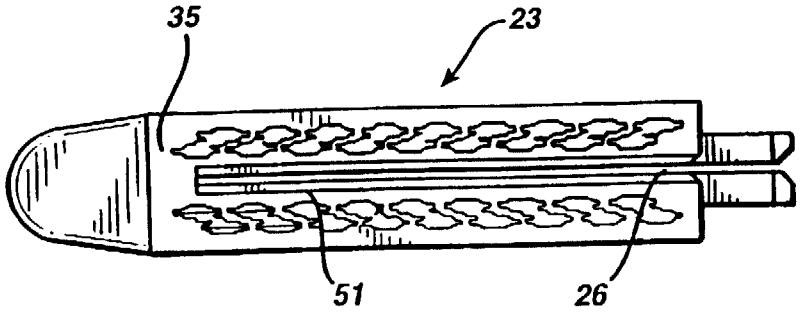
FIG. 8 is a top isolated view of a cartridge of the instrument of FIG. 1.
Figure 9:
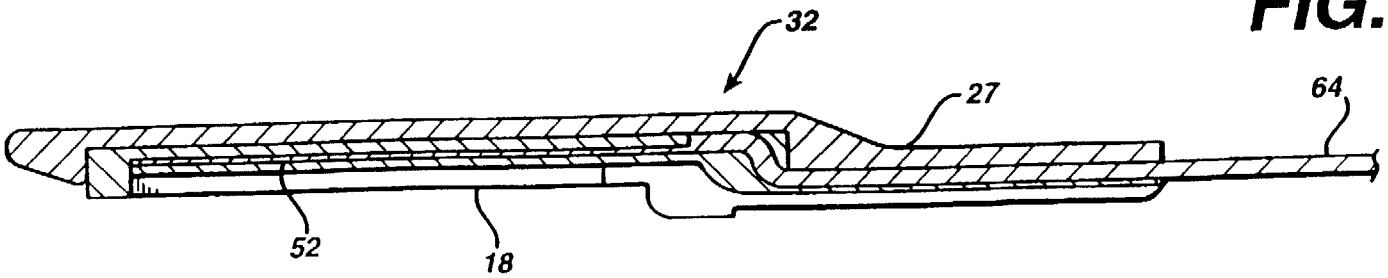
FIG. 9 is a side cross sectional view of the jaw of FIG. 7 along the line 9—9.

Referring now to FIGS. 3–9 and 22 an enlargement of the end effector 50 of the instrument 10 is illustrated. The jaw members 32 and 34 are shown in an unclamped position in FIG. 3, in a clamped, unfired position in FIG. 4 and in a clamped, fired position in FIG. 5. Jaw member 32 comprises an anvil 18, a U-shaped first pole 52 extending longitudinally with respect to the jaw 32, and a U-shaped insulating material 55 surrounding the outside of the first pole 52. Jaw member 32 has an inner surface 33 which faces an inner surface 35 of jaw 34. The inner surface 33 includes first pole 52 which comprises two electrically communicating electrode bars 53, 54 comprised of stainless steel or aluminum, extending substantially along the length of the inner surface 33. The bars 53, 54 are separated by a knife channel 42 extending longitudinally through the first pole's center to form its U-shape. The surface of the bars are formed in flat strips to provide more surface area contact with tissue. Two series of pockets 36, 37 located on anvil 18, for receiving staple ends, extend along the inner surface 33, lateral to and outside of bars 53, 54 respectively. The electrode bars 53, 54 and the insulating material 55 form a ridge 56 extending out relative to the anvil portion 33*a* of the inner surface 33 (FIG. 6). The anvil 18 is formed of an electrically conductive material and acts as a second pole electrically opposite to the first pole. The anvil 18 is isolated from the first pole 52 by the U-shaped insulating material 55.

Jaw member 34 comprises a cartridge channel 22 and a cartridge 23. The cartridge 23 includes a track 25 for the wedge 13, knife channel 26 extending longitudinally through the center of the cartridge 23, a series of drivers 24 extending into track 25 and staples 100 arranged in two sets of parallel double rows. When tissue is engaged between the jaws 32, 34, the driver means 44 may be actuated or fired using trigger 14 to advance the cutting means 11 and wedge 13 through the engaged tissue to staple and cut the tissue. When the firing mechanism 14 is actuated, the wedge 13 is advanced through the track 25 causing the drivers 24 to displace towards the staples 100, thereby driving the staples 100 through tissue and into anvil pockets 36, 37.

Figure 22:
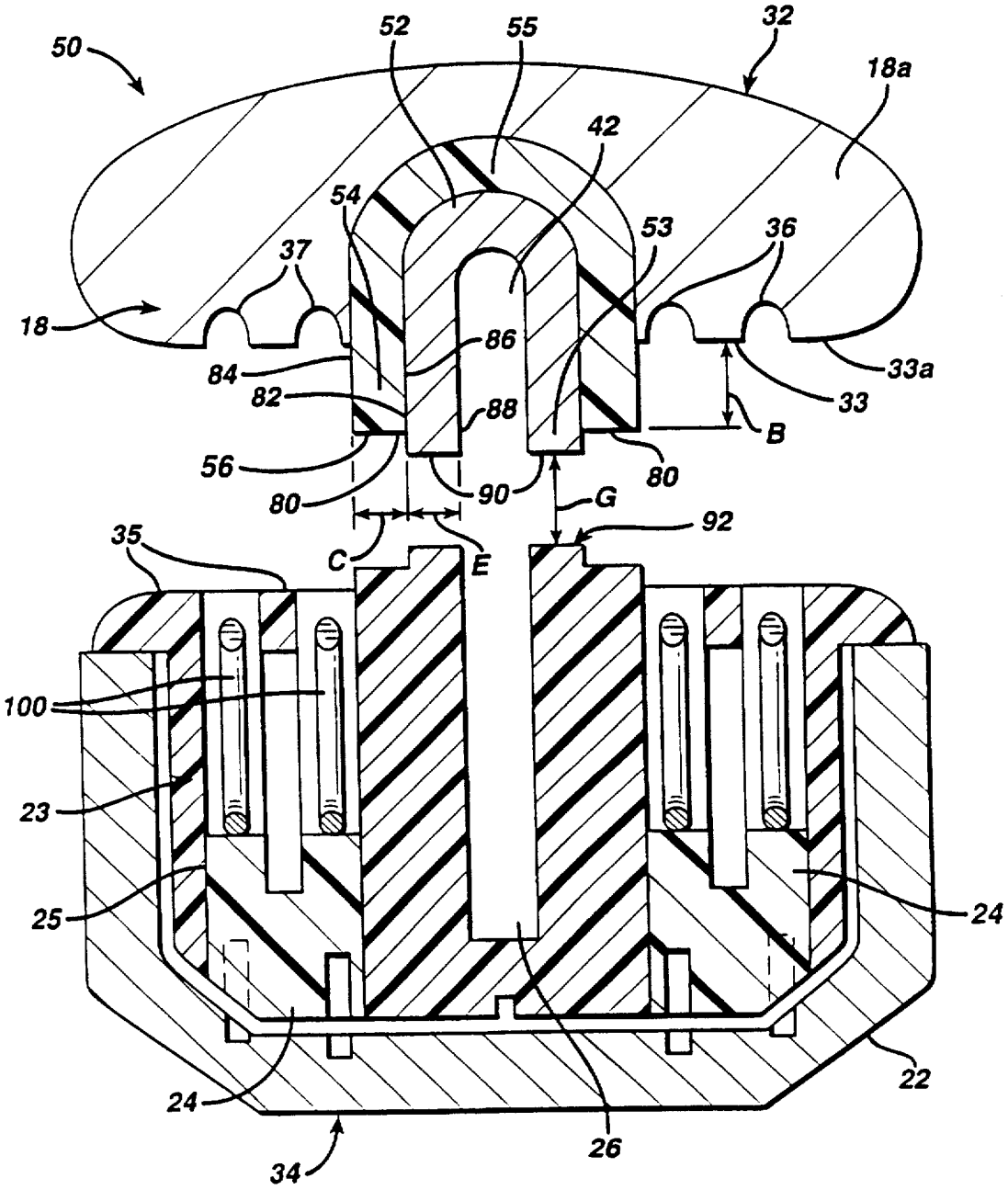
FIG. 22 is a cross sectional view of the end effector according to a further embodiment of the present invention.

In the embodiment of the invention illustrated in FIG. 22, dimension B, which is measured from inner surface 33 of jaw member 32 to tissue surface 80 of U-shaped insulating material 55, is preferably in the range of from approximately 0.0 inches to approximately 0.045 inches and preferably approximately 0.0 inches. Dimension C, which is measured from inner edge 82 to outer edge 84 of U-shaped insulator 55 along tissue surface 80, is preferably in the range of from approximately 0.01 inches to approximately 0.04 inches and preferably approximately 0.02 inches. Dimension E, which is measured from inner edge 86 to outer edge 88 of first pole 52 as measured along tissue surface 90, is preferably in the range of from approximately .002 inches to 0.04 inches and preferably approximately 0.020 inches. Dimension G, which is measured from tissue surface 90 to tissue surface 92 with jaws 32 and 34 closed, is preferably in the range from approximately 0.0 inches to approximately 0.020 inches and preferably approximately 0.001 inches. Dimension G is measured without tissue engaged.

A knob 15 located on the distal end of the body 16 rotates the shaft 30, sheath 38, channel 39 and end effector 50 which are directly or indirectly coupled to the knob 15 so that the knob 15 may be used for rotational placement of the end effector jaws 32,34.

Bipolar energy is supplied to the end effector 50 from an electrosurgical generator 60 through wires 19, 20 extending into the body 16 of the instrument. The generator 60 is user controlled by way of a footswitch 65.

Wire 19 which provides electrical current to the first pole, is coupled through a wire or other electrical contact means 61 to electrical contact 62, associated with the first pole, located on the distal end of close rack 45. Wire 20 which carries the current of the opposite pole, is coupled through a wire or other electrical contact means 66 to a disc contact 67 located at the distal end of the close rack 45 and electrically isolated from contact 62.

A disc contact 63, associated with the first pole, located at the distal end of the body 16 is in electrical communication with a wire or other contact means 64. Contact means 64 extends through channel 39 to end effector jaw 32 where it contacts first pole 52. The disc contact 63 permits the knob 15 to rotate while contact is maintained between the disc contact 63 and the contact means 64. The contact means 64 is electrically insulated from the sheath 38.

When the clamping trigger 12 is actuated, the close rack 45 moves distally so that the contact 62 comes in electrical communication with the disc contact 63 and the disc contact 67, associated with the second pole 51, comes in electrical contact with the electrically conductive sheath 38. The sheath 38 moves over the camming surface 27 of the electrically conductive anvil 18 which acts as the return electrode. Thus the electrical circuit is closed when and only when the clamping trigger 12 is closed.

In operation, the end effector 50 of the instrument is located at a tissue site where tissue is to be cut. The jaw members 32, 34 are opened by pressing a release button 70 which releases a button spring 71 and permits the close rack 45 to move proximally. Tissue is then placed between the interfacing inner surfaces 33, 35 respectively of the jaw members 32, 34. The clamping trigger 12 is squeezed to cause the sheath 38 to move over the camming surface 27 and thereby close the jaws 32, 34 and simultaneously close the electrical circuit as described above. The electrode bars 53, 54 and the insulating material 55, which together form the ridge 56, compress the tissue against the inner surface 35 of jaw member 34. A user then applies RF energy from the generator 60 using the footswitch 65 or other switch. Current flows through the compressed tissue between the first pole 52, i.e. the bars 53, 54, and the second pole 51, i.e., the anvil 18.

In one embodiment of the present invention the initial pressure applied to compress the tissue in the compression zone is between approximately 30 pounds per square inch (psi) and 250 psi. More particularly, in a further embodiment of the present invention the initial pressure applied to compress the tissue in the compression zone is between approximately 75 psi and 250 psi. More particularly in a further embodiment of the present invention the initial pressure applied to compress the tissue in the compression zone is between approximately 75 psi and 175 psi. In one embodiment of the present invention, the initial pressure applied to compress tissue positioned between the jaws is approximately 125 psi. With sufficient pressure applied fluid, including blood, is forced out of the tissue in the compression zone, facilitating coagulation. In addition, pressure applied to tissue within the compression zone facilitates coupling of electrosurgical energy to the tissue by forcing the tissue against the electrode.

The pressure exerted by the anvil is a function of the spring rate of the anvil. By providing a "pre-bend" angle on the anvil it is possible to obtain a pre-load (at a zero gap.) Thus, where a pre-bend angle is applied, the anvil may be viewed as a prestressed beam. A Preferred value of preload is in the range of between 12 and 18 pounds with a preferred value of approximately 15 pounds. The spring rate of the anvil is more accurately a function of the stiffness of the "system", where the system includes the anvil, channel, cartridge, tube, etc. Each of the elements of the system has a particular spring rate and each may be suitably modified to increase the stiffness of the system.

In one embodiment of the present invention, that the spring rate of anvil jaw 32 is between approximately 225 pounds per inch and approximately 350 pounds per inch. More particularly, the spring rate of anvil 18 on jaw 32 is preferably in the range of approximately 275 pounds per inch.

Preferably the bipolar energy source is a low impedance source providing radio frequency energy from about 300 kkHz to 3 MHZ. Preferably, the current delivered to the tissue is from 0.1 to 1.5 amps and the voltage is from 30 to 200 volts RMS.

An audible, visible, tactile, or other feedback system may be used to indicate when sufficient cauterization has occurred at which point the RF energy may be turned off. An example of such a feedback system is described below. After the RF energy is turned off, the cutting means 11 is advanced and the staples 100 are fired using the firing trigger 14. Firing is accomplished by rotating the firing trigger 14 acting as a lever arm about pivot 14*a*. The driver means 44 advances the cutting means 11 and wedge 13. The cutting means 11 cuts the tissue in between the bars 53, 54 where the tissue has been cauterized. Thus, the cut line is lateral to the coagulation lines formed by the bar electrodes. The wedge 13 simultaneously advances the drivers 24 into the staples 100 causing the staples 100 to fire through tissue and into the pockets 36, 37 of the anvil 18. Staples 100 are applied in two longitudinal double rows on each side of the cutting means 11 as the cutting means cuts the tissue.

Operation of linear staplers are known in the art and are discussed, for example, in U.S. Pat. Nos. 4,608,981, 4,633,874, and U.S. application Ser. No. 07/917,636 incorporated herein by reference.

In one embodiment the cartridge provides multifire stapling capabilities by replacing the double row of staples with a single row. In the laparoscopic stapling and cutting devices presently in use, a single shot replaceable cartridge is used. In order to provide better hemostasis, this type of stapler was designed, to provide a double row of staples for each parallel row. Because of the size of the space necessary to contain the double row of staples, a refireable cartridge with stacked staples has not been preferred because of the additional space required for stacking staples. In the multifire stapling embodiment a single row of staples is used. Using a single row of staples permits stacking of staples in the space previously occupied by the second row of staples, providing multifire capabilities. In a further embodiment, no staples are required and the electrical current lines provide the necessary hemostasis.

A preferred embodiment of the present invention includes a feedback system designed to indicate when a desired or predetermined degree of coagulation has occurred. This is particularly useful where the coagulation zone is not visible to the user. In a particular embodiment, the feedback system measures electrical parameters of the system which include coagulation level.

The feedback system may also determine tissue characteristics at or near a coagulation zone which indicate degree of coagulation. The electrical impedance of the tissue to which the electrical energy is applied may also be used to indicate coagulation. Generally, as energy is applied to the tissue, the impedance will initially decrease and then rise as coagulation occurs. An example of the relationship between electrical tissue impedance over time and coagulation is described in Vaellfors, Bertil and Bergdahl, Bjoern "Automatically controlled Bipolar Electrocoagulation," Neurosurg. Rev. p. 187–190 (1984) incorporated herein by reference. Also as desiccation occurs, impedance increases. Tissue carbonization and or sticking to instrument as a result of over application of high voltage may be prevented using a feedback system based on tissue impedance characteristics. Other examples of tissue characteristics which may indicate coagulation include temperature and light reflectance.

Figure 10:
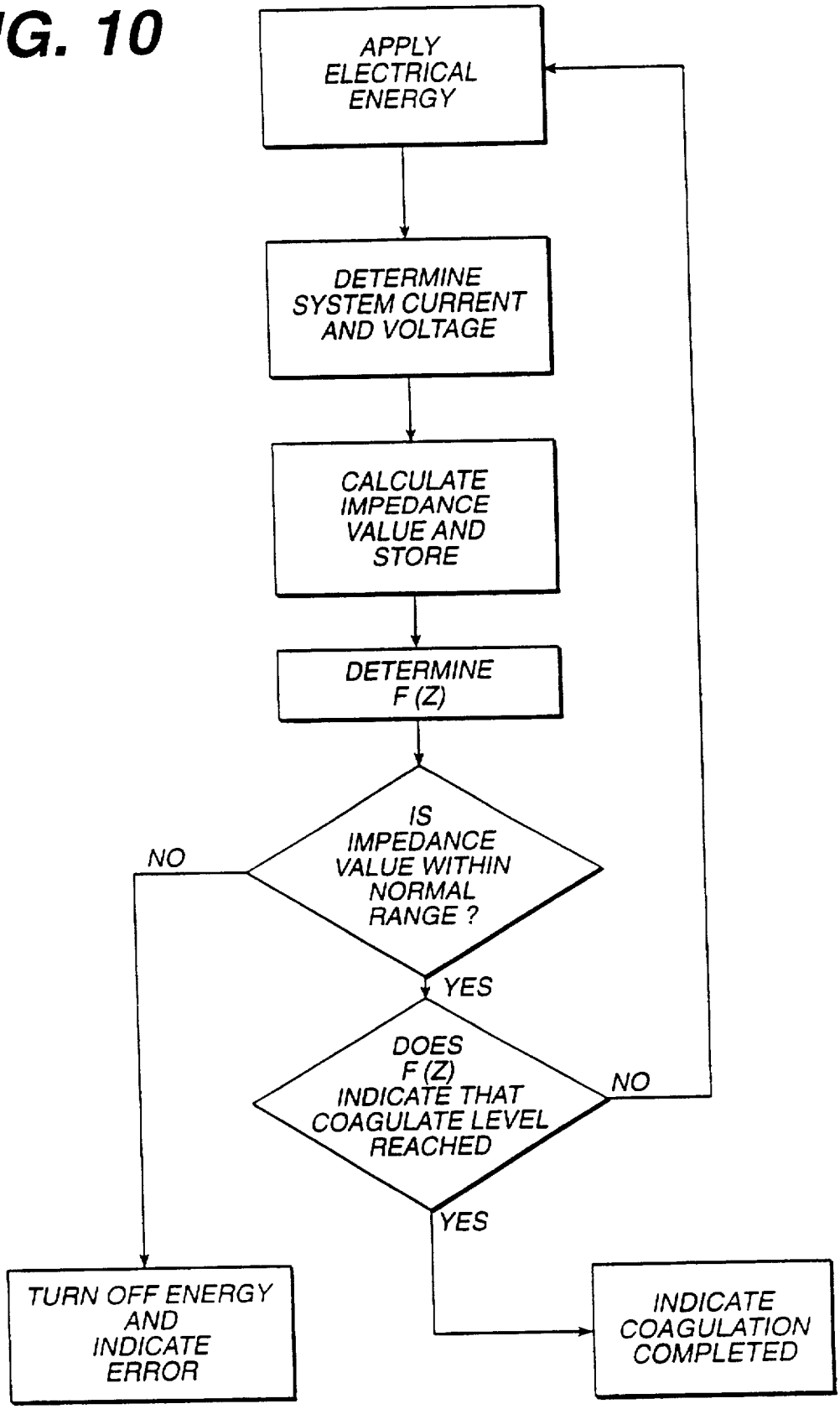
FIG. 10 is a flow chart illustrating a feedback system of the present invention.

Referring to FIG. 10, a flow chart illustrates a feedback system which is implemented in a preferred embodiment of the present invention. First, energy is applied to the tissue. Then the system current and voltage applied to the tissue is determined. The impedance value is calculated and stored. Based on a function of the impedance, for example, which may include the impedance, the change in impedance, and/or the rate of change in impedance, it is determined whether desired coagulation has occurred. If coagulation has occurred to a predetermined or desired degree, an indication means indicates that the energy should be turned off. Such an indication means may include a visible light, an audible sound or a tactile indicator. The feedback means may also control the generator and turn the energy off at a certain impedance level. An alternative embodiment provides a continuous audible sound in which the tone varies depending on the impedance level. An additional feature provides an error indication means for indicating an error or instrument malfunction when the impedance is below a normal minimum and/ or above a maximum range.

Figure 11:
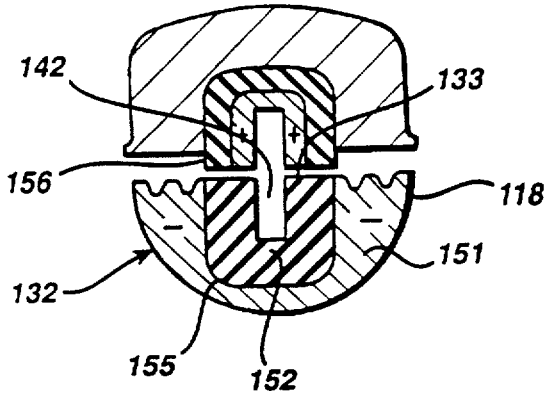
FIG. 11 is a front cross sectional view of the end effector of another embodiment of the present invention.

FIGS. 11–14 illustrate alternative configurations of an end effector. In FIG. 11 the first pole 152 and the second pole 151 are both located on the same jaw 132 having the anvil 118. The U-shaped first pole 152 forms the knife channel 142. A U-shaped insulator 155 surrounds the first pole 152 except on the surface 133 so that it is electrically isolated from the second pole 151. The compression ridge 156 is formed on the cartridge which is made from an electrically non-conductive material. The ridge 156 compresses tissue against the first pole 152 and insulator 155 to form a tissue compression zone.

Figure 12:
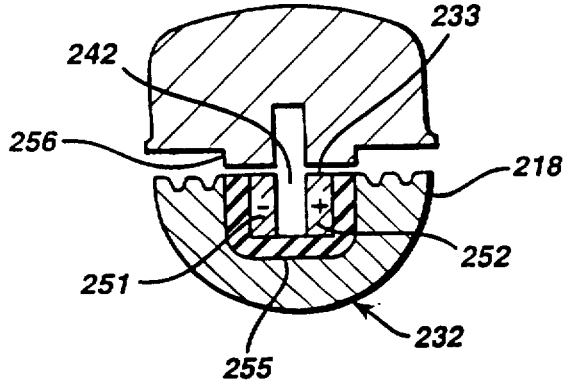
FIG. 12 is a front cross sectional view of the end effector of another embodiment of the present invention.

In FIG. 12, the first pole 252 and the second pole 251 are both located on the same jaw 232 having the anvil 218. The first pole 252 and the second pole 251 each are located on opposing sides of the knife channel 242. An insulator 255 surrounds the poles 251, 252 except on the surface 233 so that the poles 251, 252 are electrically isolated from each other. The compression ridge 256 is formed on the cartridge which is made from an electrically non-conductive material. The ridge 256 compresses tissue against the poles 251, 252 and insulator 255 to form a tissue compression zone.

Figure 13:
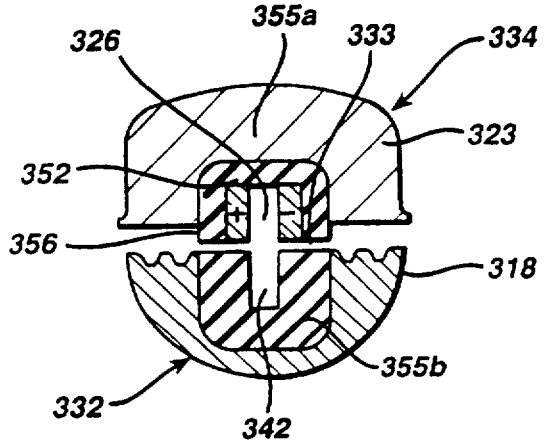
FIG. 13 is a front cross sectional view of the end effector of another embodiment of the present invention.

In FIG. 13, second pole 351 is located on the jaw 332 having the anvil 318 while the first pole 352 is located on the cartridge 323. The U-shaped first pole 352 forms the knife channel 326 and is surrounded by insulator 355*a*. A U-shaped insulator 355*b* forms the knife channel 342 in jaw 332. Except for the insulator 355*b*, the jaw is formed of an electrically conductive material which makes up the second pole 351. The first pole 352 and the insulator 355a form the compression ridge 356 which compresses tissue against the surface 333 of jaw 332 to form a compression zone. The insulator 355*b* is of sufficient width that it prevents poles 351, 352 form contacting when the jaws 332,334 are closed.

Figure 14:
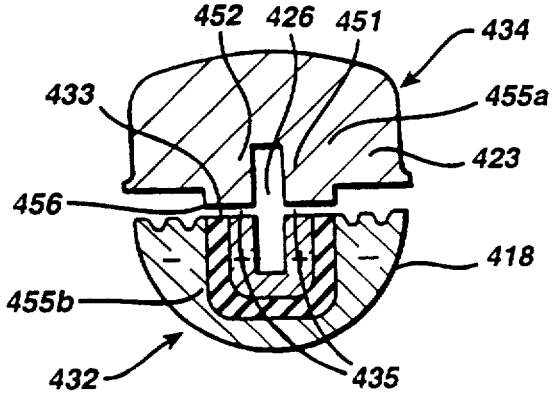
FIG. 14 is a front cross sectional view of the end effector of another embodiment of the present invention.

In FIG. 14, the first pole 452 and the second pole 451 are both located on the jaw 434 having the cartridge 423. The first pole 452 and the second pole 451 each are located on opposing sides, forming the knife channel 426 through the cartridge 423. An insulator 455*a* surrounds the poles 451, 452 except on :the surface 435, so that the poles 451, 452 are electrically isolated from each other. The compression ridge 456 is formed on the cartridge 423 and forms a compression zone by compressing tissue against an insulator 455*b* disposed on the surface 433 of the jaw 432.

Figure 15:
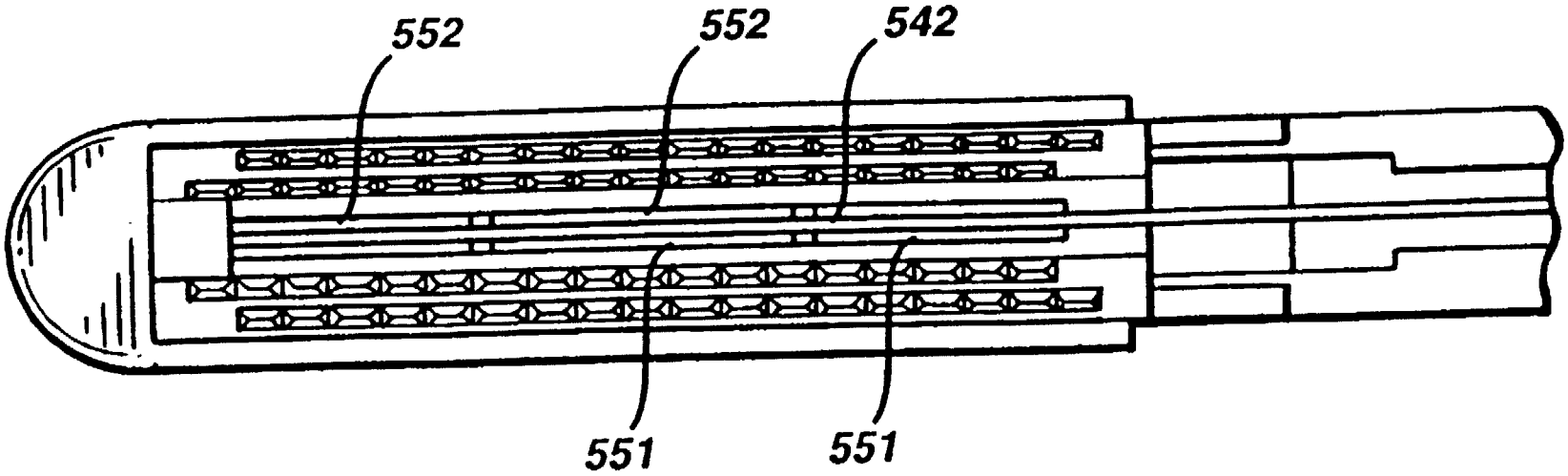
FIG. 15 is a bottom isolated view of the anvil of another embodiment of the present invention.

FIG. 15 illustrates an alternative embodiment. The first and second poles 551, 552 and knife channel 542 are arranged in a similar configuration as in FIG. 12 except that the first and second poles 551 and 552 each comprise a series of electrically connected electrodes staggered along the length of the knife channel with insulating material in between staggered electrodes.

Figure 16:
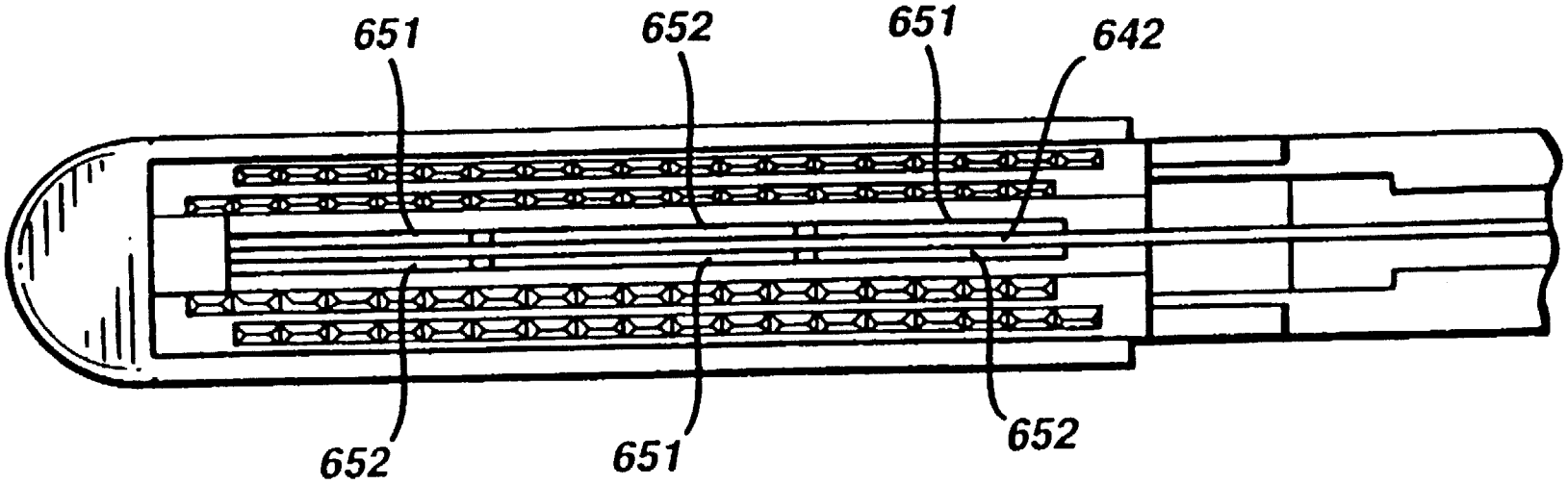
FIG. 16 is a bottom isolated view of the anvil of another embodiment of the present invention.

FIG. 16 illustrates staggered electrodes as in FIG. 15 but with first pole electrodes 652 and second pole electrodes 651 alternating along the length of the knife channel 642 and on each side of the knife channel 642.

Figure 17:
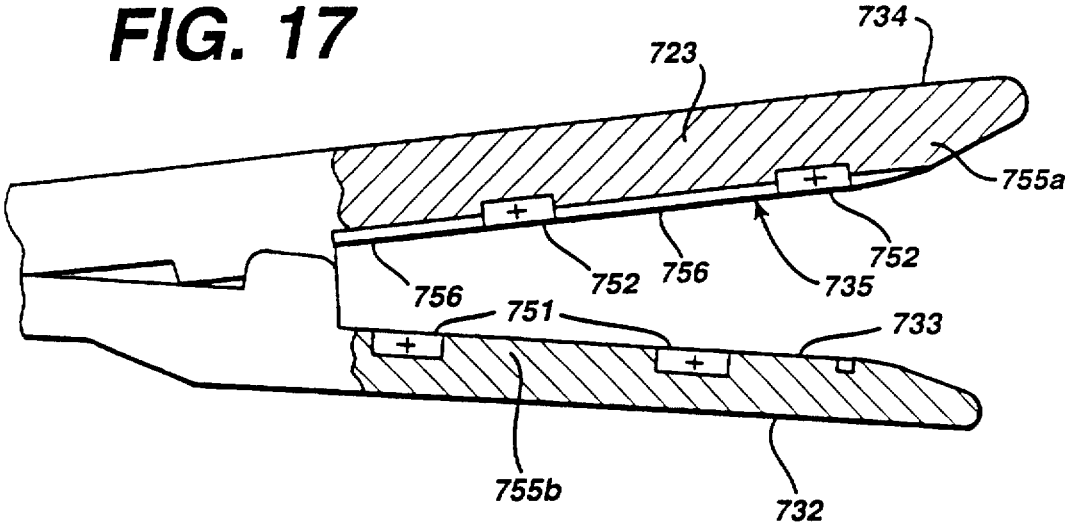
FIG 17 illustrates a cross sectional view of the distal end of another embodiment of the present invention.
Figure 18:
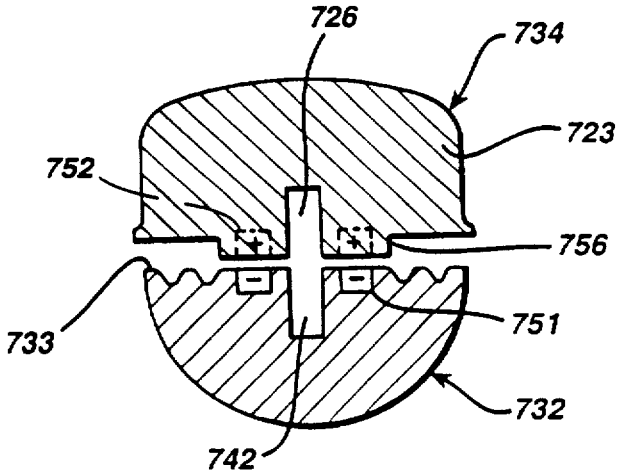
FIG. 18 is front cross sectional view of the end effector of FIG. 17.

FIGS. 17 and 18 illustrate another embodiment in which first and second poles 751, 752 each comprise staggered electrodes. In this embodiment, the first pole 752 is staggered along each side of the knife channel 126 and located on the compression ridge 756 formed on the cartridge 723. The second pole 751 is staggered along each side of the knife channel 742 on the surface 733 of jaw 732. As can be seen from FIG. 18, the poles 751, 752 are vertically aligned, but as illustrated in FIG. 17, are staggered so that when the jaws 732, 734 are closed, the poles are electrically isolated from each other by insulators 755*a*, 755*b*.

Figure 19:
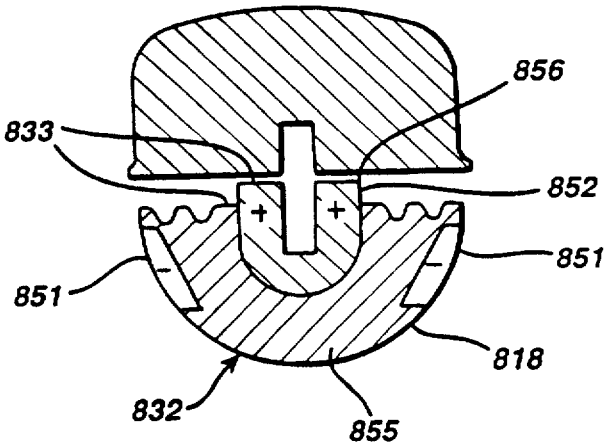
FIG. 19 is a front cross sectional view of the end effector of another embodiment of the present invention.

FIG. 19 illustrates an alternative embodiment of the end effector. The first pole 852 and the second pole 851 are both located on the jaw 832 having an anvil 818. The first pole 852 forms the ridge 856 for compressing tissue in a compression zone and is located on interfacing surface 833. The second pole 851 is located on the side of the anvil 818 and not on interfacing surface 833.

Figure 20:
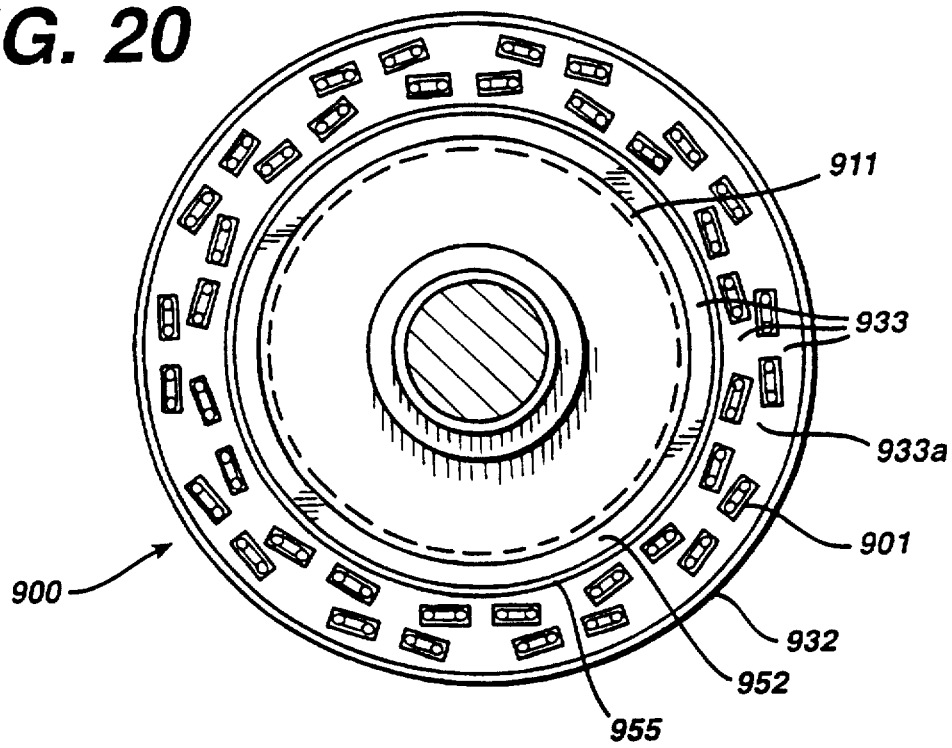
FIG. 20 is a top view of a cartridge of a circular cutter of the present invention.
Figure 21:
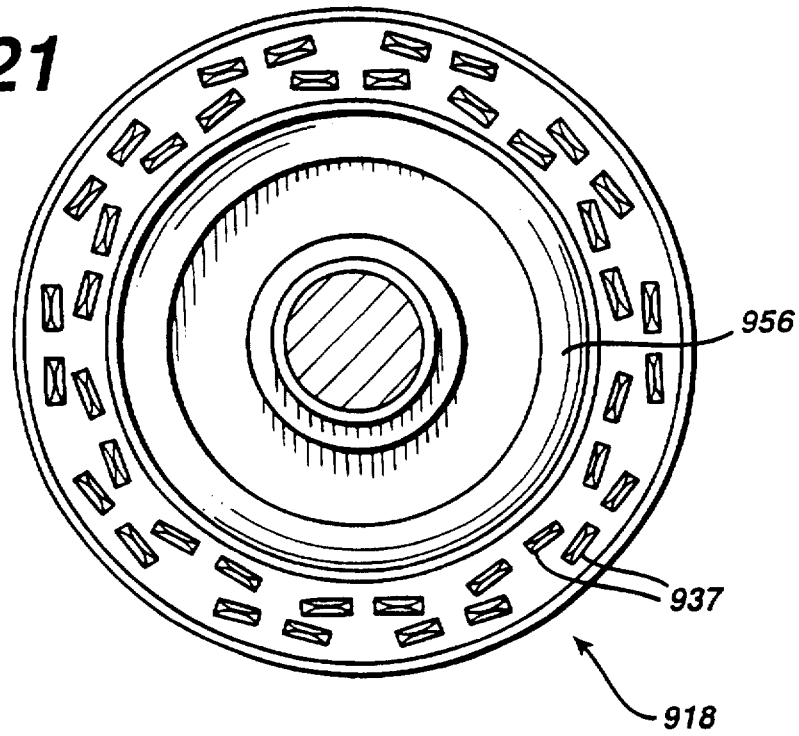
FIG. 21 is a bottom view of the anvil of a circular cutter of the present invention.

FIGS. 20 and 21 illustrate a circular cutter of the present invention with stapling means. FIG. 20 illustrates the stapler cartridge 900 with an interfacing surface 933. A double row of staple apertures 901 through which staples are driven into tissue are staggered about the outer circumference of the surface 932. A first pole 952 encircles the inner circumference of the surface 933. An insulator 955 electrically isolates the first pole 952 from the portion 933*a* of the surface 933 surrounding the staple apertures. The staple aperture portion 933*a* is formed of an electrically conductive material and acts as a second pole. A circular cutting knife 911 is recessed within the cartridge 900 radially inward from the inner circumference of the surface 933.

FIG. 21 illustrates an anvil 918 with pockets 937 for receiving staples and a compression ridge 956 for compressing tissue against the first pole 952 and insulator 955 of the cartridge. The circular cutter is operated similarly to the circular stapler described in U.S. Pat. No. 5,104,025 incorporated herein by reference. Prior to stapling and cutting however, tissue welding electrical current may be delivered between the first pole 952 and the staple aperture portion 933*a* to tissue.

In an alternative embodiment, the circular cutter may be used without staples. Electrical current is delivered through the poles to weld and coagulate tissue, then the knife may be advanced to cut tissue in a procedure such as an anastomosis.

In operation, the jaws of the instrument, for example, jaws 32 and 34 of end effector 50, are closed around the tissue which is to be treated. Tissue trapped between the instrument jaws is compressed as described herein An electrosurgical instrument according to the present invention is beneficial in that coagulation of tissue is enhanced since the pressures applied force fluid out of the coagulation region without tearing the tissue. The pressure ranges specified herein are also beneficial in that, using an instrument according to the present invention, contact between the tissue and electrodes is improved, coagulation is improved throughout the tissue and charring is reduced.

Several variations of this invention has been described in connection with two specific embodiments involving endoscopic cutting and stapling. Naturally, the invention may be used in numerous applications where hemostasis in desired. Accordingly, will be understood by those skilled in the art that various changes and modifications may be made in the invention without departing from its scope, which is defined by the following claims and their equivalents.

What is claimed is:

1. An end effector for an electrosurgical device, wherein said end effector comprises:

first and second jaw members;

first and second opposing interfacing surfaces, said interfacing surfaces being capable of engaging tissue therebetween, and said end effector capable of receiving bipolar energy therein, said first jaw comprising an anvil having a spring rate of between approximately two hundred twenty five pounds per inch and three hundred fifty pounds per inch;

electrically isolated first and second poles comprising electrically opposite electrodes capable of conducting bipolar energy therethrough; wherein said first pole is comprised of one or more first electrodes of a first electrical potential; wherein said second pole is comprised of one or more second electrodes of a second electrical potential;

wherein at least one of said one or more first electrodes is located on at least one of said first and said second interfacing surfaces and wherein at least one of said one or more second electrodes is located on at least one of said first and second interfacing surfaces, so that bipolar energy may be communicated between said poles through the tissue; and wherein each said one or more first electrodes is offset from each said one or more second electrodes, at said first and second interfacing surfaces.

2. The end effector of claim 1 wherein said spring rate is approximately two hundred and seventy five pounds per inch.

3. The end effector claim 1 wherein said anvil is pre-bent such that, when said first and second jaws are closed, with at least a portion of said first and second interfacing surfaces touching to create a zero gap, said anvil has a preload in a range of between approximately twelve pounds and eighteen pounds.

4. The end effector of claim 1 wherein a portion of said second interfacing surface comprises a ridge extending from said second interfacing surface to form a tissue compression zone between interfacing surfaces.

5. The end effector of claim 4 wherein current flowing between said first and second poles provides coagulation in the compression zone.

6. The end effector of claim 1 wherein said end effector includes a cutting element mounted on said end effector to divide tissue engaged by said end effector when said cutting element is actuated to move said cutting element through said tissue.

7. The end effector of claim 6 wherein said end effector further comprises at least one staple and at least one driver adapted to apply said at least one staple lateral to said cutting line.

8. The end effector of claim 1 wherein said one or more first electrodes comprises an electrode having a relatively circular shape and is located on an outer circumference of said first interfacing surface.

9. The end effector of claim 8 wherein said end effector includes a cutting element mounted on said end effector and being adapted to divide tissue engaged by said interfacing surfaces.

10. The end effector of claim 9 wherein said end effector further comprises at least one staple and at least one driver adapted to drive said at least one staple through tissue 11. An electrosurgical instrument comprising:

a handle, an actuating means coupled to said handle, an end effector coupled to the distal end of said actuating means, a means for communicating bipolar electrical energy from a biopolar energy source to said end effector, said end effector including:

first and second jaw members, a first interfacing surface, a second interfacing surface, a first pole comprising one or more first electrodes of a first electrical potential located on at least one of said interfacing surfaces, a second pole comprising one or more second electrodes of a second electrical potential located on at least one of said interfacing surfaces, and an insulator arranged to offset each of said one or more first electrodes from each of said one or more second electrodes, at said interfacing surfaces, wherein said actuating means is capable of causing said end effector to engage tissue between the first interfacing surface and the second interfacing surface, wherein said first jaw member is an anvil and wherein said anvil has a spring rate of between approximately two hundred twenty five pounds per inch and approximately three hundred fifty pounds per inch, wherein said first pole and said second pole are comprised of electrically opposite electrodes capable of conducting electrical energy supplied from said means for communicating bipolar electrical energy from a bipolar energy source, through tissue adjaccent to said one or more first electrodes and said one or more second electrodes.

12. The electrosurgical device of claim 11 wherein said spring rate is approximately two hundred and seventy five pounds per inch.

13. The electrosurgical device of claim 11 wherein said anvil is pre-bent such that, when said first and second jaws are closed, with at least a portion of said first and second interfacing surfaces touching to create a zero gap, said anvil has a preload in a range of between approximately twelve pounds and approximately eighteen pounds.

14. An electrosurgical instrument having an end effector, wherein said end effector comprises:

first and second opposing interfacing surfaces, said interfacing surfaces capable of engaging tissue therebetween, and said end effector capable of receiving bipolar energy therein;

a cutting element arranged on said instrument to cut tissue engaged by said end effector when said cutting element is actuated, wherein said first interfacing surface includes a first slot extending longitudinally therethrough for receiving said cutting element;

a cartridge containing at least one row of staples and at least one driver adapted to apply said staples to tissue engaged by said end effector, said cartridge having a second slot extending longitudinally therethrough for receiving said cutting element, said first and second slots arranged to permit said cutting element to travel lateral to said at least one row of staples, said cartridge forming at least a portion of said second interfacing surface;

an anvil for receiving and forming said staples, said anvil forming at least a portion of said first interfacing surface which said anvil has a spring rate of between approximately two hundred twenty five pounds per inch and three hundred fifty pounds per inch;

electrically isolated first and second poles positioned on said first interfacing surface and comprising electrically opposite electrodes, wherein said first pole is comprised of first and second elongated substantially parallel electrodes arranged on opposite sides of said first slot and said second pole comprises an electrode positioned on said anvil;

first and second compression ridges extending from said first interfacing surface, wherein said first and second electrodes comprise at least a portion of said first and second compression ridges;

third and fourth electrically insulating compression ridges extending from said second interfacing surface;

a first tissue contacting surface on said first and second compression ridges;

a second tissue contacting surface on said third and fourth compression ridges; and a recessed insulation region separating said first pole from said second pole wherein said recessed insulation region includes a recessed tissue contacting surface, said recessed tissue contacting surface being approximately level with said portion of !said first interfacing surface comprising said anvil.

15. The electrosurgical device of claim 14 wherein spring rate is approximately two hundred seventy five pounds per inch.

16. The electrosurgical device of claim 14 wherein said anvil is pre-bent such that, when said end effector is closed, with at least a portion of said first and second interfacing surfaces touching to create a zero gap, said anvil has a preload in a range of between approximately twelve pounds and eighteen pounds.

17. An electrosurgical instrument comprising:

a handle, an actuating means coupled to said handle, an end effector coupled to the distal end of said actuating means, a means for communicating bipolar electrical energy from a bipolar energy source to said end effector, said end effector comprising:

first and second opposing interfacing surfaces, said interfacing surfaces capable of engaging tissue therebetween, and said end effector capable of receiving bipolar energy therein;

a cutting element arranged on said instrument to cut tissue engaged by said end effector when said cutting element is actuated, wherein said first interfacing surface includes a first slot extending longitudinally therethrough for receiving said cutting element;

a cartridge containing at least one row of staples and at least one driver adapted to apply said staples to tissue engaged by said end effector, said cartridge having a second slot extending longitudinally therethrough for receiving said cutting element, said first and second slots arranged to permit said cutting element to travel lateral to said at least one row of staples, said cartridge forming at least a portion of said second interfacing surface;

an anvil for receiving and forming said staples, said anvil forming at least a portion of said first interfacing surface wherein said anvil has a spring rate of between approximately two hundred twenty five pounds per inch and three hundred fifty pounds per inch;

electrically isolated first and second poles positioned on said first interfacing surface and comprising electrically opposite electrodes, wherein said first pole is comprised of first and second elongated substantially parallel electrodes arranged on opposite sides of said first slot and said second pole comprises an electrode positioned on said anvil;

first and second compression ridges extending from said first interfacing surface, wherein said first and second electrodes comprise at least a portion of said first and second compression ridges;

third and fourth electrically insulating compression ridges extending from said second interfacing surface;

a first tissue contacting surface on said first and second compression ridges;

a second tissue contacting surface on said third and fourth compression ridges;

and a recessed insulation region separating said first pole from said second pole wherein said recessed insulation region includes a recessed tissue contacting surface, said recessed tissue contacting surface being approximately level with said portion of said first interfacing surface comprising said anvil.

18. The electrosurgical device of claim 17 wherein said spring rate is approximately two hundred seventy five pounds per inch.

19. The electrosurgical device of claim 17, wherein said anvil is pre-bent such that, when said end effector is closed, with at least a portion of said first and second interfacing surfaces touching to create a zero gap, said anvil has a preload in a range of between approximately twelve pounds and approximately eighteen pounds.

* * * * *